United States Patent [19]

Porteous

[11] 4,212,546

[45] Jul. 15, 1980

[54] TILTABLE POWER BLENDER FOR DENTAL IMPRESSION MATERIALS

[76] Inventor: Don D. Porteous, 2794 Moraga Dr., Los Angeles, Calif. 90024

[21] Appl. No.: 944,554

[22] Filed: Sep. 21, 1978

[51] Int. Cl.² .............................................. A61C 5/06
[52] U.S. Cl. ................................. 366/213; 241/169.1; 366/220; 366/602
[58] Field of Search .............. 366/602; 210, 211, 213, 366/220, 221, 225, 230, 231, 237, 232, 200, 129, 130; 241/169.1

[56] References Cited

U.S. PATENT DOCUMENTS

| 2,041,318 | 5/1936 | Berger | 366/230 X |
| 2,692,105 | 10/1954 | Lamb | 366/200 X |
| 3,411,755 | 11/1968 | Strauss et al. | 366/602 X |

FOREIGN PATENT DOCUMENTS

| 9520 | 9/1908 | France | 366/220 |
| 1004151 | 11/1951 | France | 366/231 |
| 1332457 | 10/1973 | United Kingdom | 366/231 |

Primary Examiner—Philip R. Coe
Attorney, Agent, or Firm—Donald Diamond

[57] ABSTRACT

A blender for dental impression materials - alginates and dental stones, for example—is provided with a multi-speed electric motor for actuating a turntable through a speed reducing geartrain. The turntable surmounts a substantially rectangular enclosure for the drive components. A handgrip for the user is provided in a narrow end of the enclosure, near a control switch for the drive motor. A flexible rubber bowl is removably mounted on the turntable and receives the materials to be blended. Elastomeric support strips along the base of the enclosure are carried over an angled rear panel of the lower half of the housing, so as to provide nonskid support means as the enclosure is tilted to facilitate the blending process by moving the rotational axis of the bowl away from the vertical.

8 Claims, 7 Drawing Figures

TILTABLE POWER BLENDER FOR DENTAL IMPRESSION MATERIALS

BACKGROUND OF THE INVENTION

This invention relates to blending devices for dental impression materials and, more particularly, to blending devices incorporating a motor driven movable bowl which may be tilted during the blending cycle.

In the field of dental work relating to the repair and replacement of natural teeth it is frequently necessary to prepare impression materials—such as alginates—in the form of a viscous slurry of substantial uniformity and free of entrapped air bubbles. An analogous requirement exists in the mixing of dental stone, fine-textured plasters, with which the impressions taken in the aforementioned alginates are cast to form models of the mouth cavity.

Due to the relatively high viscosity of such slurries and the need for speed and precision in performing the blending of the raw powders and the binding agent, commonly water, the manual preparation of such materials has heretofore been a major obstacle in the taking of dental impressions and the subsequent processing of the impressions obtained.

It is, therefore, a primary object of this invention to provide externally powered means for blending and mixing the materials required in the dental arts.

It is a further object of this invention to provide a blending device for dental impression materials which incorporates constructional features to facilitate the ease of operation and to effect minimal expenditure of time and effort in performing the blending task.

It is yet another object of this invention to provide a blender for dental impression materials in which the rotational axis of the mixing bowl may be readily tilted for greater control of the blending process and ease of handling.

SUMMARY OF THE INVENTION

The foregoing objects, and other objects and advantages of the invention which shall become apparent in the detailed description of the preferred embodiment thereof, are attained in a device powered by means of a fractional-horsepower electric motor located within a substantially rectangular enclosure, formed of upper and lower housing halves interlocked along an equatorial beltline.

The electric motor is directly coupled to a rightangle reducing gear drive whose output shaft passes through the upper surface of the aforementioned enclosure and upon which a turntable is mounted, surmouting the upper housing half. A mixing bowl, preferably constructed of a flexible elastomeric substance, is engaged upon said turntable in a removable manner.

Handle means, integral with a frontal panel of the lower housing half, are provided for the operator of the blender. The enclosure is provided with support means, in the form of elastomeric strips affixed to the distal surface of the lower housing half; one pair of said support stips is continued over at least a portion of the rear panel of the lower housing half and provides nonskid support for the blender when the frontal portion thereof is elevated by means of the integral handle to tilt the rotational axis of the bowl mounted on the turntable.

DESCRIPTION OF THE PREFERRED EMBODIMENT

Figure 1:
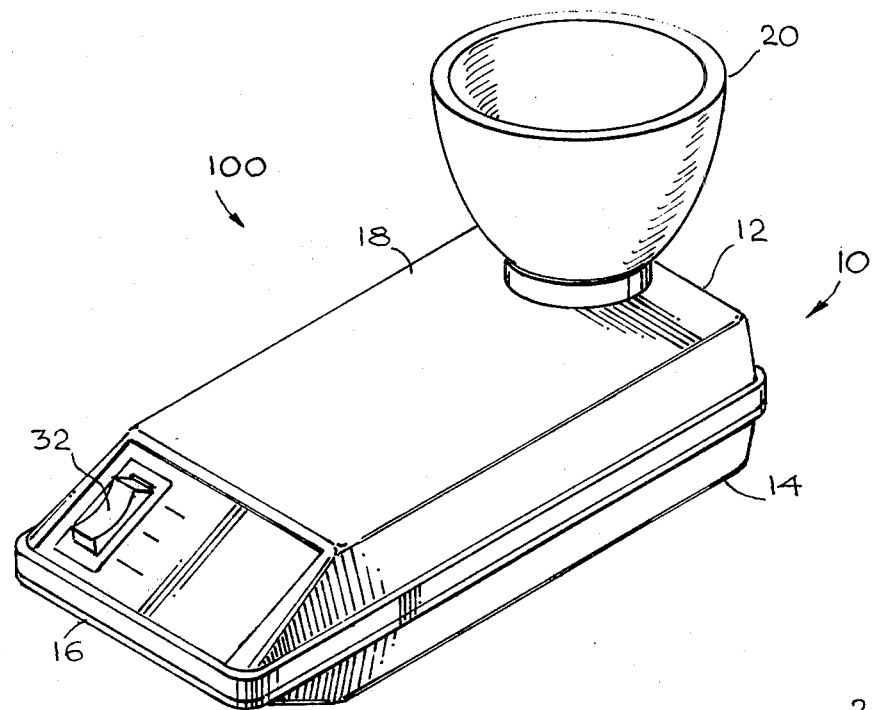
FIG. 1 is a perspective view of a blending device for dental impression materials constructed in accord with the principles of the invention.
Figure 6:
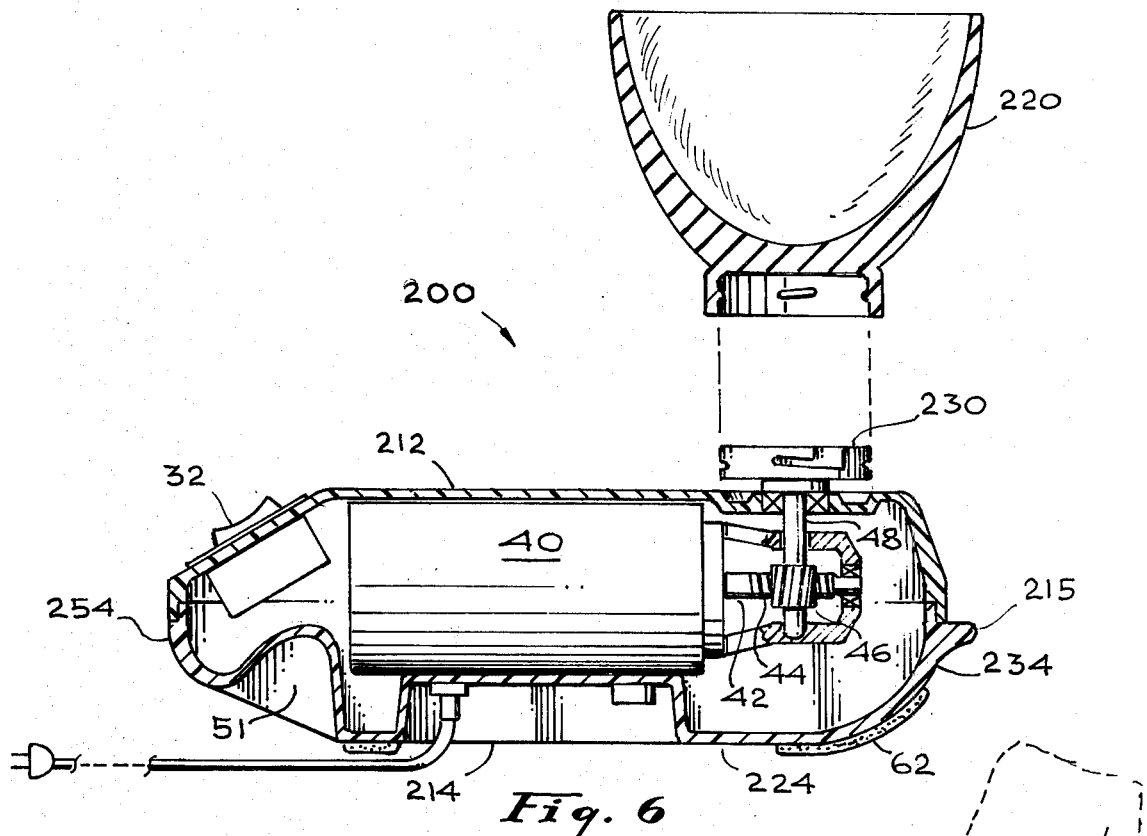
FIG. 6 is a lateral section taken through another embodiment of the invention, illustrating details of the drive means therein.

The perspective view of FIG. 1 depicts a dental blending device 100 with an enclosure 10 composed of upper and lower housing halves 12 and 14 interlocked along an equatorial beltline 16. A rotatable bowl 20 surmounts the upper housing half 12, whose top surface 18 is pierced, at a locus near the rear end 19 of the enclosure, by a driveshaft 48 (as shown in FIG. 6) upon which a turntable 30 is affixed; the bowl 20 is engagable, by means of mutually interlocking protruberances, with the turntable 30.

The blending device 100 is principally utilized in converting powdered impression materials—such as alginates—into smooth pastes by intermixing the powders with water. In this process it is extremely important that the volume and pore size of entrained air be reduced as much as possible and that the resulting slurry be as uniform as attainable. Prior to the availability of the blending device 100 the perparation of such materials required tedious mixing manually with a spatula. Not only is such manual preparation time and energy consuming, but considerable skill has to be developed to yield the desirable quality of product.

Figure 5:
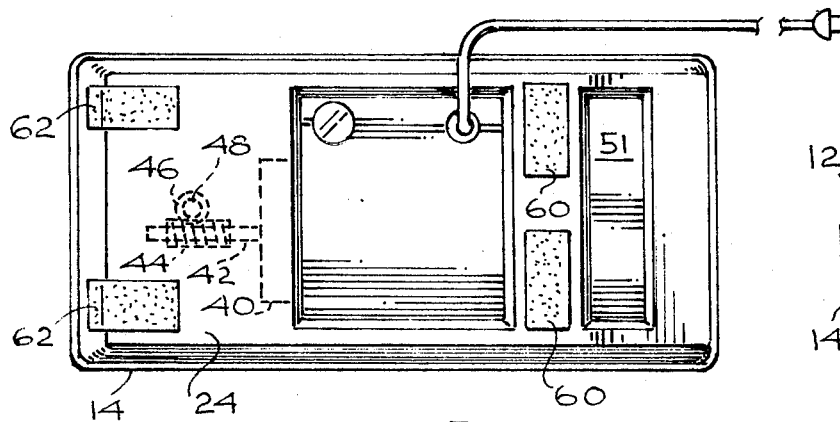
FIG. 5 is a bottom plan view of the embodiment of FIG. 1 with the gear drive being shown in phantom lines.

In the device 100 the raw materials are charged into the bowl 20, roughly mixed with a few strokes of a hand-held spatula, and the device turned on by operating a switch 32. An electric motor 40, located within enclosure 10, rotates the bowl and causes the contents to become mixed, partly by centrifugal distribution of the material along the inner surface of the bowl and partly by interaction with the spatula which the user holds within the cavity of the bowl. The device, as shown in FIGS. 2, 5 and 6, is equipped with an appropriate fuse and and an electrical cord for providing current to the motor from a wall socket.

The enclosure 10 is provided with a handgrip defined by oblique frontal panels of the upper and lower housing halves and by a cavity 51 formed within frontal panel 54 of the lower housing half 14. This handgrip is utilized by the user to tilt the blending device 100 to an angle, commonly approaching 45 degrees from the horizontal, at which it is easiest for him to control the interaction of the spatula held in his other hand and the contents of the bowl 20. The blending process is also aided, in the preferred mode of construction by the provision of at least two motor speeds, controlled by switch 32, so as to adjust the conditions of intermixing to the particular material and the desired viscosity of the mix.

Figure 2:
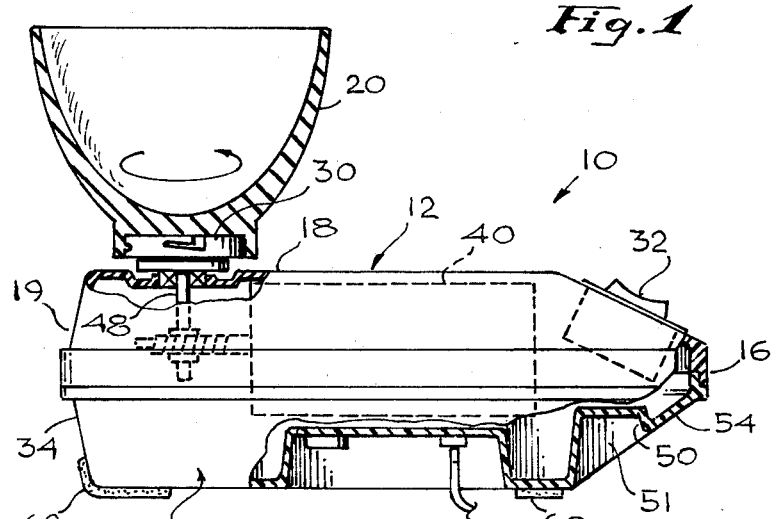
FIG. 2 is a left side elevational view of the device of FIG. 1 partially broken away and in section to show major components and motor mounting platform.

The side elevation of FIG. 2 illustrates the manner in which the side and end panels of the upper and lower housing halves, typified by a frontal or first end panel 54 of the lower housing half 14, form internal obtuse angles with upper and lower surfaces 18 and 24 of the enclosure 10, so that the dimensions of the enclosure are largest along the beltline 16.

Figure 3:
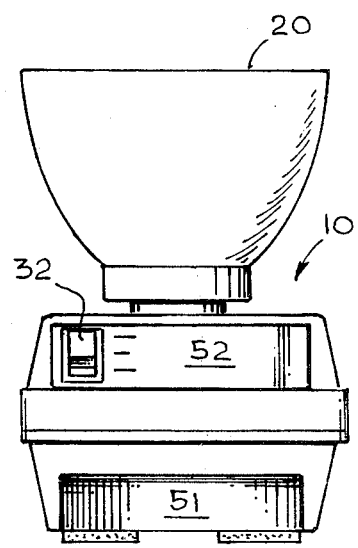
FIG. 3 is a frontal elevational view of the embodiment of FIGS. 1 and 2.

The frontal view of FIG. 3 shows the location of the aforementioned handhold in frontal panel 54 of the lower housing half, delimited by a partition 50, as well as the relative location of motor control switch 32 in frontal panel 52 of the upper housing half 12.

Figure 4:
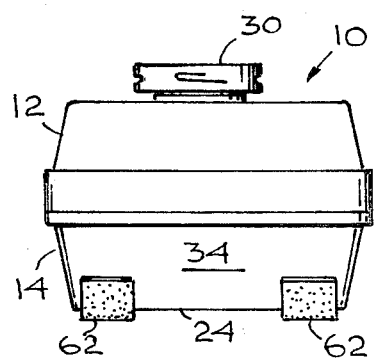
FIG. 4 is a rear elevational view of the device of the foregoing Figures.

The rear view of FIG. 4 and the base view of FIG. 5 illustrate the manner in which elastomeric support strips 60 and 62 are affixed to the distal surface of base panel 24 of the lower housing half 14. The elastomeric support strips 62 at the rear of enclosure 10 follow the base and are continued for some distance over the outer surface of the rear or second end panel 34 of the lower housing half, so as to provide nonskid support means for the blending device 100 even with the latter tilted with respect to the supporting surface on a worktable or counter.

FIG. 6 is a lateral section taken through a modified embodiment 200 of the blending device of the invention, showing the several components of the drive system therein, including an electric motor 40, motorshaft 42, worm 44 and mating worm-gear 46, and driveshaft 48. A turntable 230 is mounted on driveshaft 48 and supports a bowl 220 for rotation through motor 40. The lateral view of this Figure is particularly adapted to show the manner in which handhold 51 is integrated into frontal panel 254 of a lower housing half 214. The lower housing half 214 mates with an upper housing half 212 to form an enclosure analogous to the enclosure 10 of the embodiment of FIGS. 1 through 5. A rear panel 234 of the lower housing half 214 is provided with a substantial internal obtuse angle, of the order of 135 degrees, with respect to basal surface 224 and a bumper 215 in provided integral therewith near the portion mating with the upper housing half.

Figure 7:
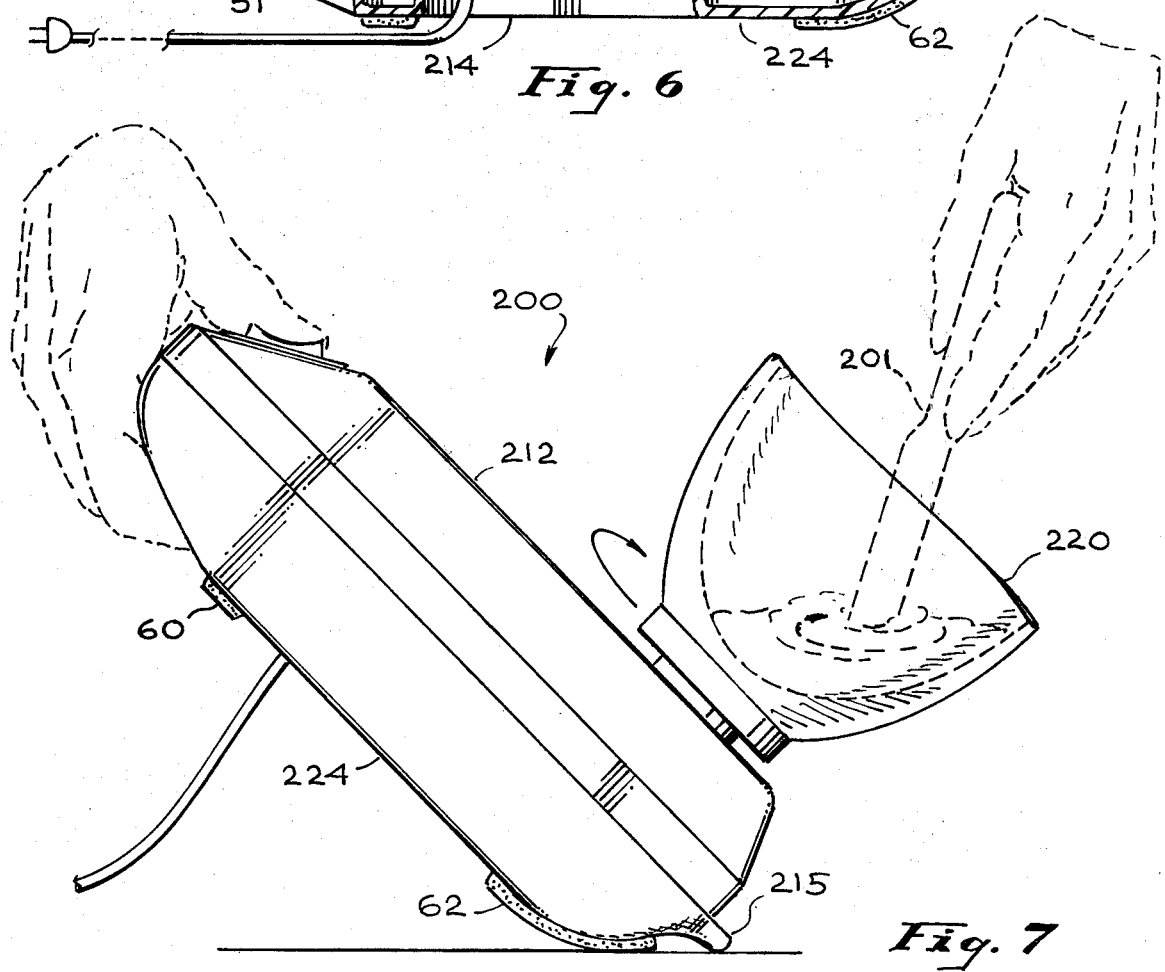
FIG. 7 is a view, in elevation, of the device of FIG. 6 in the tilted position assumed during the blending cycle.

As shown in the lateral view of FIG. 7, when the blender 200 is in use, it may be tilted to an angle approaching 45 degrees from the horizontal rest position by pivoting the blender on support strips 62 around the point of intersection of base and rear panels 224 and 234, until the bumper 215 contacts the working surface upon which the blender is positioned. This angular tilt greatly facilitates the blending process and permits the suitable positioning of a spatula 201 within the bowl 220. The position of the spatula, as shown in FIG. 7, is schematic. It is advantageous, during the mixing process, to place the spatula in close alignment with the inner wall of the bowl to provide a locus of higher mechanical shear to assist mixing, to disintegrate lumps, and to facilitate the elimination of air bubbles.

To assist in the removal of mixed materials therefrom, and in the subsequent cleaning of the bowl 220, it is constructed from a flexible elastomer by preference.

While in the foregoing description and accompanying drawing there has been shown and described the peferred embodiment of this invention, it will be understood, of course, that minor changes may be made in the details of construction as well as in the combination and arrangement of parts without departing from the spirit and scope of the invention as claimed.

That which is claimed is:

1. A blending device for dental impression materials comprising:

a substantially rectangular enclosure which includes upper and lower housing halves interlocked along a beltline, said upper housing half having an upper surface conjoint with oppositely disposed side panels and oppositely disposed first and second end panels, said lower housing half having a lower surface conjoint with oppositely disposed side panels and oppositely disposed first and second end panels;

drive means disposed within said enclosure, said drive means including an electric drive motor coupled to a rotational drive shaft through a speed reducing geartrain, said driveshaft passing trough, and in substantially orthogonal alignment with, the upper surface of said upper housing half;

a turntable mounted on said driveshaft, said turntable being disposed above and spaced from said upper surface;

a bowl member removably engaged upon said turntable;

control means for said drive means;

handle means integral with said first end panel of said lower housing half; and support means, including elastomeric support strips, affixed to the lower surface of the lower housing half of said enclosure.

2. The blending device of claim 1, wherein said control means includes a switch located proximate to said handle means, for connecting said drive motor to a source of electrical current.

3. The blending device of claim 2, wherein said electric motor is adapted to multispeed operation and said switch includes means for selecting motor operating speed.

4. The blending device of claim 3, wherein said speed-reducing geartrain includes a worm and a worm-gear mating therewith.

5. The blending device of claim 4, wherein said support means include at least one pair of elastomeric support strips disposed near said first end panel of said lower housing half, and at least one pair of elastomeric support strips disposed adjacent to said second end panel and continuing upwardly over the second end panel of said lower housing half.

6. The blending device of claim 5, wherein said support means additionally comprise bumper means affixed to said second end panel proximate to said beltline.

7. The blending device of claim 5, wherein said bowl means includes a mixing bowl constructed from an elastomeric material.

8. The blending device of claim 5 wherein each of the first and second end panels of the lower housing half is disposed at an obtuse angle with respect to the lower surface of said lower housing half.

* * * * *